US006639090B2

(12) United States Patent
Ramey et al.

(10) Patent No.: US 6,639,090 B2
(45) Date of Patent: Oct. 28, 2003

(54) POWDERED OVERBASED AMORPHOUS ALKALINE EARTH METAL SALTS AND PROCESSES FOR MAKING

(75) Inventors: Chester E. Ramey, Chagrin Falls, OH (US); James E. Reddy, Lyndhurst, OH (US)

(73) Assignee: OMG Americas, Inc., Westlake, OH (US)

( * ) Notice: Subject to any disclaimer, the term of this patent is extended or adjusted under 35 U.S.C. 154(b) by 0 days.

(21) Appl. No.: 10/379,048

(22) Filed: Mar. 4, 2003

(65) Prior Publication Data

US 2003/0158054 A1 Aug. 21, 2003

Related U.S. Application Data

(63) Continuation-in-part of application No. 09/861,393, filed on May 18, 2001.

(51) Int. Cl.$^7$ .............................................. C07C 51/00
(52) U.S. Cl. ...................... 554/156; 554/157
(58) Field of Search ................. 554/156, 157

(56) References Cited

U.S. PATENT DOCUMENTS

| | | | | |
|---|---|---|---|---|
| 2,616,904 A | 11/1952 | Asseff et al. | ................ | 260/399 |
| 2,760,970 A | 8/1956 | Le Suer | ................ | 260/429 |
| 2,767,164 A | 10/1956 | Asseff et al. | ................ | 260/139 |
| 2,798,852 A | 7/1957 | Wiese et al. | ................ | 252/42.7 |
| 2,802,816 A | 8/1957 | Asseff et al. | ................ | 260/139 |
| 2,971,014 A | 2/1961 | Mastin | ................ | 260/398 |
| 2,989,463 A | 6/1961 | Mastin | ................ | 252/25 |
| 3,027,325 A | 3/1962 | McMillen et al. | ................ | 252/33 |
| 3,031,284 A | 4/1962 | Andress, Jr. et al. | ................ | 44/76 |
| 3,147,232 A | 9/1964 | Norman et al. | ................ | 260/23 |
| 3,194,823 A | 7/1965 | Le Suer et al. | ................ | 260/414 |
| 3,342,733 A | 9/1967 | Robbins et al. | ................ | 252/33 |
| 3,533,975 A | 10/1970 | Scullin | ................ | 260/23 |
| 3,766,066 A | 10/1973 | McMillen | ................ | 252/32.7 |
| 3,766,067 A | 10/1973 | McMillen | ................ | 252/33 |
| 3,773,664 A | 11/1973 | Lesuer | ................ | 252/40.7 |
| 3,779,922 A | 12/1973 | LeSuer | ................ | 252/34.7 |
| 4,159,973 A | 7/1979 | Hoch et al. | ................ | 260/23 XA |
| 4,252,698 A | 2/1981 | Ito et al. | ................ | 260/18 EP |
| 4,665,117 A | 5/1987 | Quinn | ................ | 524/327 |
| 5,147,917 A | 9/1992 | Sugawara et al. | ................ | 524/257 |
| 5,259,966 A | 11/1993 | Burke, Jr. et al. | ................ | 252/18 |
| 5,322,872 A | 6/1994 | Quinn | ................ | 524/186 |
| 5,501,807 A | 3/1996 | Benda et al. | ................ | 252/18 |
| 5,519,076 A | 5/1996 | Odaira et al. | ................ | 524/112 |
| 5,534,169 A | 7/1996 | Vinci | ................ | 508/460 |
| 5,830,832 A | 11/1998 | Benda et al. | ................ | 508/460 |
| 5,830,935 A | 11/1998 | Khattar et al. | ................ | 524/114 |
| 5,859,267 A | 1/1999 | Khattar et al. | ................ | 554/4 |

FOREIGN PATENT DOCUMENTS

WO    WO99/10307    *    3/1999

\* cited by examiner

Primary Examiner—Deborah D. Carr
(74) Attorney, Agent, or Firm—Wood, Herron & Evans, L.L.P

(57) ABSTRACT

Powdered overbased amorphous alkaline earth salts are made which consist essentially of isolated solid agglomerated micelles of amorphous alkaline earth metal salts complexed with an amorphous alkaline earth metal carboxylate of a fatty acid. The process for making the powder involves precipitating and isolating the solid particles from liquid overbased alkaline earth metal compositions.

46 Claims, No Drawings

POWDERED OVERBASED AMORPHOUS ALKALINE EARTH METAL SALTS AND PROCESSES FOR MAKING

RELATED APPLICATIONS

This application is a continuation-in-part application of U.S. patent application Ser. No. 09/861,393, filed on May 18, 2001. The entire disclosure of that application is incorporated herein by reference.

FIELD OF THE INVENTION

The present invention relates to powdered overbased amorphous alkaline earth metal salts of fatty acids and a process for producing them. The overbased powders are useful in many applications including polymer stabilizers, lubricants, catalysts, oil well compositions, animal nutrition and cosmetics.

BACKGROUND OF THE INVENTION

The preparation of overbased calcium or barium salts of carboxylic acids, alkyl phenols, and sulfonic acids are disclosed in the following U.S. Pat. Nos.: 2,616,904; 2,760,970; 2,767,164; 2,798,852; 2,802,816; 3,027,325; 3,031,284; 3,342,733; 3,533,975; 3,773,664; and 3,779,922. The use of these overbased metal salts in the halogen-containing organic polymer is described in the following U.S. Pat. Nos.: 4,159,973; 4,252,698; and 3,194,823. The use of overbased barium salt in stabilizer formulations has increased during recent years. This is due, in the main, to the fact that overbased barium salts possess performance advantages over the neutral barium salts. The performance advantages associated with overbased barium salts are low plate-out, excellent color hold, good long-term heat stability performance, good compatibility with the stabilizer components, etc. Unfortunately, most of the overbased barium salts are dark in color and, while these dark colored overbased barium salts are effective stabilizers for halogen-containing organic polymer, their dark color results in the discoloration of the end product. This feature essentially prohibits the use of dark colored overbased barium salts in applications where a light colored polymer product is desired.

According to the teachings of U.S. Pat. No. 4,665,117, light colored alkali or alkaline earth metal salts are prepared where alkyl phenol is used as a promoter. However, alkyl phenol is also a major cause for the development of color in the final product. This problem is overcome by the use of propylene oxide which displaces the hydrogen of the phenolic hydroxyl group and thereby restricts the formation of colored species. However, there are disadvantages associated with this approach, principally due to the toxic nature of propylene oxide. Propylene oxide is classified as a possible carcinogen and laboratory animal inhalation studies have shown evidence of a link to cancer. Propylene oxide is also listed as a severe eye irritant, and prolonged exposure to propylene oxide vapors may result in permanent damage to the eye. Furthermore, propylene oxide is extremely flammable and explosive in nature under certain conditions. Propylene oxide boils at 94° F. and flashes at −20° F. As a result, extreme precautions are required to handle propylene oxide at the plant site. Special storage equipment is required for propylene oxide and other safety features are necessary. U.S. Pat. No. 4,665,117 describes the use of propylene oxide at 150° C. At this temperature, propylene oxide will be in the gaseous phase. Under these operating conditions, more than stoichiometric amounts of propylene oxide are required to carry the reaction to completion because propylene oxide will escape from the reaction mixture and this requires additional handling of the excess propylene oxide.

With the movement in the plastics industry to remove heavy metals, liquid calcium-zinc stabilizers are desirous, but not practical, as replacements for barium-cadmium or barium-zinc. Low metal concentrations, poor compatibility, haziness in clear products and plate out during processing in PVC have severely limited the universal acceptance of calcium based liquid stabilizer compositions. Problems are encountered in the stability of these compositions upon standing or storage. Storage stability is due to the incompatibility among the metal salts employed in the composition and is exhibited by increased turbidity, viscosity, or insoluble solids over time. As a result, the liquid calcium compositions are no longer homogeneous or readily pourable and must be specially treated in order to be used. U.S. Pat. No. 5,322,872 is directed to stabilized compositions of mixed metal carboxylates having improved storage stability. According to this patent, a complexing agent is added to the mixed metal carboxylate in order to improve shelf stability. Complexing agents disclosed in this patent include phosphines, phosphites, aromatic cyanides, aromatic hydroxy compounds, oximes and other compounds. U.S. Pat. Nos. 5,830,935 and 5,859,267 have also issued as directed to processes for improving basic metal salts and stabilizing halogen-containing polymers therewith.

U.S. Pat. Nos. 3,766,066 ('066) and 3,766,067 ('067) disclose the preparation of solid calcium-containing micellar complexes from homogenized carbonated calcium overbased organic acid salts with the aid of "conversion agents" such as water and alcohols. The '067 patent teaches that to prepare the desired micellar complexes from the overbased salts it is first necessary to subject a solution of those salts in inert organic liquid diluents to a homogenization step with vigorous agitation in the presence of water, alcohols or mixtures of alcohols and water. The homogenization is accompanied by a "thickening" or "gelling" phenomenon to produce crystalline particles characterized by an x-ray diffraction pattern corresponding to that of calcite. However, x-ray diffraction studies of the starting salt solutions do not indicate the presence of any crystalline calcium carbonate. In fact, the '066 patent teaches that the calcium carbonate present in the starting non-homogenized solution appears to be amorphous. The amorphous metal salts or complexes present in the material are unquestionably transformed to crystalline particles on homogenization according to the '066 and '067 patents. U.S. Pat. No. 5,534,169 also teaches the conversion of a Newtonian overbased calcium carboxylate to a non-Newtonian dispersion of calcite particles in order to produce a material useful for reducing friction. U.S. Pat. No. 5,830,832 also discloses the preparation of powdered calcium overbased soaps from branched oxo-acids.

Notwithstanding the state of the art as exemplified by the above patents, there is a need for further improvements in overbased alkaline earth metal salts of fatty acids, methods for making them and their use in product applications.

SUMMARY

The present invention relates to a powdered overbased amorphous alkaline earth metal salt of a fatty acid. These powders comprise isolated solid agglomerated particles of an amorphous alkaline earth metal salt from the group consisting of carbonate, sulfate, sulfide and sulfite complexed with an amorphous alkaline earth metal carboxylate of a fatty acid. In a preferred form, the powders are alkaline earth metal carboxylates/carbonates. These powders are referred to sometimes hereinafter more simply as "powdered overbased amorphous alkaline earth metal salt(s)" or "powdered overbased amorphous alkaline earth metal carboxylate (s)/carbonate(s)". Powdered overbased amorphous calcium and barium salts are preferably provided and, in a preferred form of the invention, the powders are essentially free of a phenol or a phenolic derivative. The powdered amorphous overbased salts are essentially solid particles which are agglomerated micelles of the amorphous metal salt, like the metal carbonate, complexed with the amorphous metal carboxylate. The agglomerated particles generally range from about 50 microns in size.

The invention also relates to a process for preparing the powdered overbased amorphous alkaline earth metal salts. The process involves reacting an alkaline earth metal base and a fatty acid with an equivalent ratio of metal base to fatty acid being greater than 1:1 in the presence of a liquid hydrocarbon. A surfactant and catalyst are used to promote the reaction. The mixture is acidified, preferably by carbonation, to produce an amorphous alkaline earth metal carbonate. In a preferred method, during carbonation, a dispersion of alkaline earth metal base, a liquid hydrocarbon, and an aliphatic alcohol having at least 8 carbon atoms, is added in relative amounts to produce a stable haze free liquid reaction product. Water is removed from the reaction product to obtain a shelf stable haze free liquid overbased alkaline earth metal salt. The powdered overbased amorphous salt is then isolated by adding a sufficient amount of solvent for the liquid hydrocarbon/alcohol of the haze free liquid to cause particles of the overbased amorphous salt to agglomerate and separate. The agglomerated particles are then isolated by filtration and drying to a state that particles are handleable as a solid powder.

As reported in our earlier application Ser. No. 09/861,393, filed on May 18, 2001, it has been found important during carbonation to add the dispersion of metal base, liquid hydrocarbon and aliphatic alcohol in relative amounts at a controlled rate to produce the stable haze free liquid reaction product. There are a number of reasons which are believed to contribute to the formation of a stable haze free liquid which is then filterable to remove impurities and byproducts of the reaction. Up to the discoveries made in accordance with the principles of this invention, it was not considered possible to make in a practical or commercial operation an overbased calcium fatty acid salt, for example, that may be filtered at commercial or practical rates to remove unwanted impurities and byproducts of the reaction to produce a shelf stable haze free liquid. In contrast, it has been found that by the continuous addition of the dispersion or slurry of base du ring carbonation, such results are achievable. It is believed that the metal base slurry prevents the formation of undesirable calcium carbonate crystals or byproducts in the desired overbased metal salt. These undesirable moieties prevent the formation of stable haze free products which are filterable. In other words, the metal base slurry is added at a controlled rate which does not exceed the rate of the desired product-forming reaction. The reaction is controlled by continuous or incremental addition of the metal base to make the calcium ions immediately available for the desired reaction as opposed to allowing the metal base, for example lime, to react and form a byproduct. Excessive byproduct or lime coated with calcium carbonate is believed to render the liquid product unfilterable. Using this procedure, the pH is controlled during the reaction so that the fatty acid is neutralized and the pH rises to about 10–12 with the continued addition of base to produce dissolved metal ion which reacts with $CO_2$ during carbonation to produce the desired product. It is believed if the reaction rate is not controlled, and the base is not dissolved, then solid base reacts or is coated with calcium carbonate to form undesirable byproducts. The formation of undesirable byproducts of the reaction renders the final product unstable and unfilterable.

It has now been found that powdered overbased amorphous salts may be produced from the haze free liquids of the overbased alkaline earth metal fatty acid salts. These powders are suitable for use in many products, including lubricants, catalysts, oil well compositions, animal nutrition and cosmetics. They are particularly useful in making mixed metal stabilizer compositions with zinc, cadmium or alkyltin carboxylates. Other metal compound stabilizers that are well known may be used where the metal component can also be barium, calcium, strontium, lead, bismuth or antimony, and mixtures thereof. The mixed metal stabilizer compositions provide heat and/or light stability to vinyl halide resins such as polyvinyl chloride (PVC), and the like.

A number of benefits are obtained by the powdered products and processes of this invention. The powders provide shelf stable overbased alkaline earth metal fatty acid salts. In particular, shelf stabilities are achieved with the powders being free of phenol and phenolic derivatives such as phenolic reaction products. This is an especially desirable advantage in view of the efforts of the trade to reduce or eliminate such phenolic products because of environmental concerns. Also, as developed above, such phenols are a source of color development. In addition, enhanced shelf stability for the powders and mixed metal stabilizer compositions of the invention have been demonstrated over presently commercially available products. In particular, presently available liquid overbased calcium fatty acid carboxylates exhibit the development of turbidity or haze, whereas the powdered compositions of this invention remain stable over extended periods of time. The isolated powders of this invention also allow easy handling and storage. The powders may be dispersed in liquid hydrocarbons and other solvents to form haze free liquids. Thus, the redispersion of the powders is not restricted to certain media. The promoters and reaction diluents are removed from the powders. Also, higher concentrations of up to about 25% of calcium, for example, are achievable upon redispersion. When the mixed metal stabilizer systems containing powdered overbased barium or calcium carboxylates are employed in vinyl halide polymers, they exhibit better compatibilities with improvements in thermal stability, clarity and plate out resistance.

In contrast to overbased crystalline powders where, for example, the crystalline needles or platelets adversely increase the viscosities or rheologies of end use products such as lubricating oils and emollients, the overbased amorphous powders of this invention offer significantly improved properties of neutralization of acidic moeities without adversely affecting viscosities in end uses. Improved detergency in end uses are also achieved by the new amorphous powders of this invention.

The above advantages, benefits and further understanding of this invention will be apparent with reference to the following detailed description and preferred embodiments.

DETAILED DESCRIPTION AND PREFERRED EMBODIMENTS

A. Powdered Overbased Amorphous Salts Derived From Shelf Stable Haze Free Liquids of Overbased Alkaline Earth Metal Salts In one preferred form of the invention, the powdered overbased amorphous salts are derived from a shelf stable haze free liquid of an amorphous overbased alkaline earth metal salt of a fatty acid which comprises an alkaline earth metal carbonate,
an alkaline earth metal carboxylate of a fatty acid,
a liquid hydrocarbon, and
an aliphatic alcohol having at least 8 carbon atoms, with the liquid being preferably free of a phenol or a phenolic derivative such as a phenolic reaction product.

In another form of the invention, the amorphous alkaline earth metal sulfate, sulfide or sulfite may be formed instead of the carbonate where the acidic gas used in the process is sulfur dioxide, sulfur trioxide, carbon disulfide, or hydrogen sulfide.

The powdered overbased amorphous salt is isolated by precipitation from the liquid overbased salts using a solvent or liquid precipitating agent, such as isopropyl alcohol, for the liquid hydrocarbon and/or alcohols and glycols which may be present, to cause solid particles of the overbased salts to form by agglomeration of the amorphous particles. The agglomerated particles of the overbased salts are then obtained by filtration and drying. It is preferred to precipitate the solids from the liquid salts to eliminate the need to distill volatiles or use specialized equipment to particulate and collect the powder, for example, by spraying. The agglomerated particle sizes for the overbased amorphous salts range from about 50 microns, although particle size is not considered critical. It has also been found that these powders are dispersible in liquid hydrocarbons and other solvents to prepare haze free liquids which have a wide variety of end uses, as reported hereinafter.

Other solvents, or liquid precipitating agents, such as methanol, ethanol, propanol, butanol, and glycol ethers may be used to precipitate the powders or agglomerated particles from the liquid overbased salts. The lower alcohols are preferred because they are more readily removed from the filtered product by drying. Such solvents or liquids have been used as "conversion agents" to convert the Newtonian overbased liquids to non-Newtonian colloidal systems with the separation of crystalline calcite particles as disclosed in U.S. Pat. Nos. 3,766,066 and 3,766,067, as stated in the above background of this invention. In contrast, according to this invention, the overbased amorphous salts have been isolated by the addition of an excessive amount of the solvent for the liquid hydrocarbon and alcohol phase of the haze free overbased liquids. It has been found, by so treating the haze free overbased liquids of this invention, that powdered overbased amorphous salts can be isolated in contrast to the crystalline calcite-containing powders of the mentioned prior patents. Thus, when the solvents are added in sufficient amounts of about 5 to 1 of the haze free overbased liquids, the overbased amorphous salts agglomerate to produce the powdered overbased amorphous products of this invention. The process is believed to be solvent extraction of the liquid hydrocarbons from the liquid overbased compositions.

The fatty acid of the overbased liquid carboxylate is generally a $C_{12}$–$C_{22}$ fatty acid, including, for example, lauric, myristic, palmitic, stearic, archidic and behenic, among the saturated fatty acids. Unsaturated fatty acids include palmitoleic, oleic, linoleic, and linolenic. Among these fatty acids, oleic is presently preferred in preparing the overbased liquid carboxylates.

The alkaline earth metal of the salt is selected from the group consisting of calcium, barium, magnesium and strontium. For example, powdered overbased calcium oleates have been prepared. These powdered overbased calcium salts contain amorphous calcium carbonate complexed with calcium oleate.

In the method of making the liquid overbased salts from which the powdered amorphous salts are derived, it is important to have an aliphatic alcohol having at least 8 carbon atoms, more preferably an alcohol having 8 to 14 carbon atoms, such as, isodecanol, dodecanol, octanol, tridecanol and tetradecanol. Isodecanol is presently preferred. It has been found that when a higher aliphatic alcohol is employed in making the liquid overbased product, phenol may be excluded from the reaction as a promoter. This is a particularly advantageous feature of the invention where it is undesirable to have a phenol or phenolic reaction product involved in the manufacture or use of the powdered overbased amorphous salts.

While not being strictly bound by theory, the liquid overbased alkaline earth salt of the fatty acid is believed to be a thermodynamically stable microemulsion. The microemulsion has micelles and a continuous phase. The micelles consist of an amorphous alkaline earth metal carbonate and an amorphous alkaline earth metal carboxylate of the fatty acid. The continuous phase of the microemulsion consists of the liquid hydrocarbon and the aliphatic alcohols or glycols which may be present. This invention is directed to isolating particles which are the agglomerated micelles of the amorphous salts to form the powdered overbased salts.

Powdered overbased amorphous metal salts have been prepared containing at least 8% by weight or more of the alkaline earth metal up to about 70% by weight. In the case of the overbased calcium salts, up to about 8% by weight calcium are produced and, for barium salts, up to about 30% by weight barium may be produced. In the preparation of higher overbased products, for example, containing about 15–70% by weight metal, it has been found suitable to use a glycol or a glycol ether along with the higher aliphatic alcohol. A glycol or glycol ether may be selected from the group consisting of diethylene glycol monobutyl ether (butyl Carbitol®), triethylene glycol, dipropylene glycol, diethylene glycol monomethyl ether, ethylene glycol monobutyl ether, and mixtures thereof.

B. The Basic Process and Critical Features of Making the Overbased Liquids and Powders Derived Therefrom The process of the present invention for preparing a shelf stable haze free liquid of an overbased alkaline earth metal salt of a fatty acid comprises reacting an alkaline earth metal base and a fatty acid with an equivalent ratio of metal base to the fatty acid being greater than 1:1 in the presence of a mixture of liquid hydrocarbon. A surfactant and catalyst promote the reaction. The mixture is acidified and preferably carbonated to produce amorphous alkaline earth metal carbonate. During carbonation, a dispersion is added containing alkaline earth metal base, liquid hydrocarbon and an aliphatic alcohol having at least 8 carbon atoms in relative amounts at a controlled rate of base addition to produce a stable haze free liquid reaction product. Water is removed from the reaction product to produce a shelf stable haze free liquid overbased alkaline earth metal salt. Generally, it is preferred that the entire process be conducted in the absence of free oxygen and, for this purpose, an atmosphere of nitrogen is used.

As developed above, one of the important features of the method is the step of adding during carbonation a dispersion of alkaline earth metal base, liquid hydrocarbon and an aliphatic alcohol having at least 8 carbon atoms at a controlled rate of base addition to produce the stable haze free liquid. It has been found that the addition of a dispersion of the base in the liquid hydrocarbon and aliphatic alcohol protects or passivates the base, thereby enabling the formation of a stable haze free liquid reaction product. By protecting or passivating the base, carbonation proceeds to produce amorphous alkaline earth metal carbonate. Unexpectedly, the reaction proceeds without the need to remove water during the reaction and results in a very stable haze free liquid reaction product. At the end of the reaction, water is removed, preferably to the level of less than 1%, more preferably less than 0.3% or 0.1%, in the obtainment of the shelf stable liquid overbased salt. The removal of water which is added during the reaction or formed by the reaction is necessitated because it forms a separate phase which impedes either the product of the reaction or the formation of a shelf stable haze free liquid.

Other features of the method include filtering the product of the reaction to produce a shelf or thermodynamically stable liquid at a product filtration rate of at least about 300 ml per 10 minutes. In a preferred form of the invention, the product which is produced is filterable to remove unwanted byproducts and enhance the shelf stability of the overbased liquid. For example, with a Buchner funnel having a 15 cm diameter under vacuum of about 25–30 inches Hg with a Whatman No. 1 filter and a diatomaceous filtering aid (Celite®512–577), the product is filterable at satisfactory rates. One of the important discoveries of the method of this invention is the ability to filter the reaction product to form a stable haze free liquid at filtration rates which heretofore were unachievable. This was especially the case when higher levels of metal content in the overbased liquids were desired, especially overbased calcium liquids. Thus, filtration removes undesirable impurities including silica, iron oxide and other metal species, unreacted calcium hydroxide, calcium carbonate, and other oxides which may contribute to lack of stability. These byproducts or impurities may comprise up to about 6% of byproduct of the reaction.

Throughout this specification and claims, the term "basic" or "overbased" as applied to the alkaline earth metal salts is used to refer to metal compositions wherein the ratio of total metal contained therein to the fatty acid moieties is greater than the stoichiometric ratio of the neutral metal salt. That is, the number of metal equivalents is greater than the number of equivalents of the fatty acid. In some instances, the degree to which excess metal is found in the basic metal salt is described in terms of a "metal ratio". Metal ratio as used herein indicates the ratio of total alkaline earth metal in the oil-soluble composition to the number of equivalents of the fatty acid or organic moiety. The basic metal salts often have been referred to in the art as "overbased" or "superbased" to indicate the presence of an excess of the basic component.

The process of the present invention may be used to prepare shelf stable liquids and isolated powders of the amorphous alkaline earth metal carboxylates of the fatty acids. As stated above, the method may be practiced without the use of phenol promoter or phenolic reaction product. Therefore, liquid and powdered overbased barium fatty acid carboxylates have been made without the need for a phenol or phenolic reaction product in order to achieve a shelf stable haze free liquid. In the case of liquid and powdered overbased calcium fatty acid carboxylates, shelf stable products are obtained without a phenol where the aliphatic alcohol having at least 8 carbon atoms is employed.

The alkaline earth metal bases utilized as a reaction component may be derived from any alkaline earth metals and, of these, calcium and barium bases are particularly preferred. The metal bases include metal oxides and hydroxides and, in some instances, the sulfides, hydro sulfides, etc. While a phenolic component or reactant may preferably be excluded from a reaction, in the case of liquid overbased calcium products, the phenol or alkyl phenol may be included to yield liquid overbased products. As stated above, the fatty acids, or mixtures thereof, as identified above may be used in the reaction mixture. For example, a surfactant that facilitates the reaction is the alkaline earth metal carboxylate of the fatty acid that is formed in situ. Other surfactants may be included, for example, general purpose surface active agents identified under the trademark Tween which are polyoxyethylene derivatives of fatty acid partial esters of sorbitol anhydrides, particularly mono- and di-oleates of the ethoxylated sorbitol, and polyisobutylene succinic acid. Furthermore, it is desirable to include a catalyst to facilitate the speed of the reaction such as propionic acid, citric acid, acetic acid and adipic acid. The hydrocarbon liquid employed in the process and the liquid reaction products generally includes any hydrocarbon diluent. Most generally, the liquid hydrocarbon is selected from the group of an oil, mineral spirits and non-aromatic hydrocarbons.

C. Amounts of Reactants and Catalysts

The amount of alkaline earth metal base utilized in the preparation of basic salts is an amount which is more than one equivalent of the base per equivalent of fatty acid or organic moiety, and more generally, will be an amount sufficient to provide at least three equivalents of the metal base per equivalent of the acid. Larger amounts can be utilized to form more basic compounds, and the amount of metal base included may be any amount up to that amount which is no longer effective to increase the proportion of metal in the product. When preparing the mixture, the amount of fatty acid and the alcohol included in the mixture is not critical except that the ratio of equivalents of the metal base of the combination of the other components in the mixture should be greater than 1:1 in order to provide a basic product. More generally, the ratio of equivalents will be at least 3:1. In those instances where phenol may be present in making an overbased calcium, the ratio of equivalents of monocarboxylic acid to phenol should be at least about 1.1:1; that is, the monocarboxylic acid is present in excess with respect to the phenol.

The ranges of hydrocarbon oil, aliphatic alcohol (preferably isodecanol), butyl Carbitol and triethylene glycol have been selected such that, in the presence of the alkaline earth fatty acid salt (i.e. Ca oleate) which acts as a primary surfactant, the mixture forms a stable inverse microemulsion of the metal carbonate, water, and surfactant (internal phase) and surfactant, cosurfactant, and hydrocarbon (external continuous phase).

The acceptable ratios of hydrocarbon oil to cosurfactant aliphatic alcohol (isodecanol) are about 2:1 to about 4:1, with about 2:1 preferred. The glycol ethers may be used at about 1–15% of the final product, butyl Carbitol preferably at about 6%, and triethylene glycol at about 0–2%, preferably at about 0.6%.

The lime slurry which is added to the oleic acid in the reaction is formulated to be an easily pumpable mixture with the general composition of about 40–50% lime, about 25–40% hydrocarbon oil, about 10–25% isodecanol, and about 0–10% butyl Carbitol. The butyl Carbitol amount that is needed to make a pumpable slurry increases as the % lime in the slurry increases.

The reaction mixture for an overbased calcium oleate, after addition of the slurry and carbonation with carbon dioxide, preferably has

| | |
|---|---|
| Ca oleate (surfactant) | about 15–30% |
| Ca carbonate | about 9–35% |
| Hydrocarbon oil | about 30–35% |
| Isodecanol (cosurfactant) | about 15–18% |
| Butyl Carbitol | about 4–6% |
| Triethylene glycol | about 0–0.8% |

The catalyst, propionic acid or a lower aliphatic mono, di, or tricarboxylic acid is used in the amount of about 0–0.1% of the final reaction mixture.

Substitution of magnesium, strontium, or barium for calcium in the overbased salt is done on an equivalent basis of the metal hydroxide. On the basis of the final reaction mixture, the following amounts may be used:

| | |
|---|---|
| $Ca(OH)_2$ (lime) | about 15–30% |
| $Mg(OH)_2$ | about 12–24% |
| $Sr(OH)_2$ | about 25–50% |
| $Ba(OH)_2$ | about 35–50% |

The step of carbonation involves treating the mixtures described above with an acidic gas in the absence of free oxygen until the titratable basicity is determined using phenolphthalein. Generally, the titratable basicity is reduced to a base number below about 10. The mixing and carbonation steps of the present invention require no unusual operating conditions other than preferably the exclusion of free oxygen. The base, fatty acid and liquid hydrocarbon are mixed, generally heated, and then treated with carbon dioxide as the acidic gas, and the mixture may be heated to a temperature which is sufficient to drive off some of the water contained in the mixture. The treatment of the mixture with the carbon dioxide preferably is conducted at elevated temperatures, and the range of temperatures used for this step may be any temperature above ambient temperature up to about 200° C., and more preferably from a temperature of about 75° C. to about 200° C. Higher temperatures may be used such as 250° C., but there is no apparent advantage in the use of such higher temperatures. Ordinarily, a temperature of about 80° C. to 150° C. is satisfactory.

By the term "acidic gas" as used in this specification and in the claims is meant a gas which upon reaction with water will produce an acid. Thus, such gases as sulfur dioxide, sulfur trioxide, carbon dioxide, carbon disulfide, hydrogen sulfide, etc., are exemplary of the acidic gases which are useful in the process of this invention. Of these acids, sulfur dioxide and carbon dioxide are preferred, and the most preferred is carbon dioxide. When carbon dioxide is used the alkaline earth carbonate is formed. When the sulfur gases are used, the sulfate, sulfide and sulfite salts are formed.

D. Halogen-Containing Polymer

A halogen-containing polymer, such as a vinyl halide resin, most commonly stabilized with the basic metal salts of this invention is polyvinyl chloride. It is to be understood, however, that this invention is not limited to a particular vinyl halide resin such as polyvinyl chloride or its copolymers. Other halogen-containing resins which are employed and which illustrate the principles of this invention include chlorinated polyethylene, chlorosulfonated polyethylene, chlorinated polyvinyl chloride, and other vinyl halide resin types. Vinyl halide resin, as understood herein, and as appreciated in the art, is a common term and is adopted to define those resins or polymers usually derived by polymerization or copolymerization of vinyl monomers including vinyl chloride with or without other comonomers such as ethylene, propylene, vinyl acetate, vinyl ethers, vinylidene chloride, methacrylate, acrylates, styrene, etc. A simple case is the conversion of vinyl chloride $H_2C=CHCl$ to polyvinyl chloride $(CH_2CHCl—)_n$, wherein the halogen is bonded to the carbon atoms of the carbon chain of the polymer. Other examples of such vinyl halide resins would include vinylidene chloride polymers, vinyl chloride-vinyl ester copolymers, vinyl chloride-vinyl ether copolymers, vinyl chloride-vinylidene copolymers, vinyl chloride-propylene copolymers, chlorinated polyethylene, and the like. Of course, the vinyl halide commonly used in the industry is the chloride, although others such as bromide and fluoride may be used. Examples of the latter polymers include polyvinyl bromide, polyvinyl fluoride, and copolymers thereof.

Metal compound heat stabilizers of vinyl halide resin compositions are well known. These metal compounds serve to capture HCl liberated during heat processing of the vinyl halide resin composition into its final shape. The metal can be lead, cadmium, barium, calcium, zinc, strontium, bismuth, tin, or antimony, for example. The stabilizers are usually metal salts of a carboxylic acid, advantageously of a $C_8$–$C_{24}$ carbon chain link monocarboxylic acid such as lauric, oleic, stearic, octoic, or similar fatty acid salts. Metal salts of alkyl phenates may be used. Mixed metal salts of such acids, and their preparation, are familiar to those skilled in the art to which this present invention pertains. Mixed metallic carboxylates involving calcium/zinc or barium/zinc blends alone and in combination with other stabilizers or additives such as beta-diketones, phosphite salts and phenolic antioxidants have been used. The metal stabilizer is a mixed metal salt of a carboxylic acid. Mixed metal salts of such acids, and their preparation, are also familiar to those skilled in the art to which this present invention pertains.

E. End Uses for the Liquid or Powdered Products

As stated above, the liquid or powdered products of this invention may be used in a number of end products such as lubricants, catalysts, oil well compositions, animal nutrition and cosmetics. Other specific examples include: wall covering, flooring (vinyl tile and inlay), medical devices, dip coating, chair mat, banner film, pigment dispersion, vinyl siding, piping, fuel additive, cosmetic, ceiling tile, roofing film, wear layer, play balls or toys, teeter, fencing, corrugated wall panels, dashboards, and shifter boots.

For example, liquid and powdered overbased amorphous metal carboxylates of the following Examples can be used in the following applications.

1. Liquid and powdered products can be used in PVC stabilizer components with high metal concentration. The powdered materials can either be used as is in powdered stabilizers, or easily dispersed in mineral oil to produce a concentrated stabilizer component with only the mineral oil as a diluent.
2. The dispersed powdered products can be used as nanoparticle templates to create microporous substrates with holes of defined size, about 0.1 μm in diameter. Other nanoparticle applications include reinforcing or non-reinforcing fillers for plastics, and radiopaque but visually clear fillers (Ba) for medical applications.
3. Dispersed into oil and fuel, the powdered product can be used in a lubricant oil as a detergent and acid neutralizer.
4. The overbased amorphous calcium oleate powder, made in a non-toxic formulation, can be used as a fat mimetic. The material has an amorphous mineral core (calcium carbonate) with a fatty acid coating.

5. The powdered overbased calcium oleate/carbonate can be used as a high calcium content dietary supplement for animal or human nutrition. The small particle size, and fatty acid salt coating on the particles makes the material more palatable and active than uncoated calcium carbonate. The material can also serve to neutralize excess stomach acid.
6. The small size, the fatty acid coating, and the solid nature of the particle makes it suitable as an ingredient in skin care products as an emollient and acid neutralizer.
7. Dispersed in a suitable carrier, the liquid and powder can be used in metalworking lubricant formulations.
8. The liquid and powdered products can be used as lubricant additives in oil well drilling applications in drilling mud formulations.
9. The liquid and powdered products can be used in oil recovery fluids, flooding fluids, spotting fluids, fluid loss components of drilling muds, and cementing fluids in oil well operations.
10. In combination with a cationic water-soluble polymer (hydrogel), the powder can be used as an oil spill absorber, oil absorbing component of air filters to improve indoor air quality.
11. The powder can be used as a component of a coating formulation, to improve the water-repellency and anti-corrosion qualities of the film.

The following Examples illustrate the preparation of the haze free liquid overbased salts (Examples 1–6 and 10) and the powdered overbased amorphous metal salts derived therefrom (Examples 7–9 and 11–12) in accordance with the method of the present invention. These examples are not considered to be limiting the scope of this invention. Unless otherwise indicated in the following examples and elsewhere in the specification and claims, all parts and percentages are by weight, and all temperatures are in degrees Fahrenheit.

EXAMPLE 1

10% Overbased Calcium Oleate/Carbonate

A phenol-free 10% overbased calcium oleate/carbonate was prepared according to this Example. A mixture of 308.42 g of oleic acid (1.100 moles), 213.15 g mineral oil, 154.14 g of isodecyl alcohol, 63.08 g of butyl Carbitol, 8.70 g of triethylene glycol, 26.97 g of water and 0.87 g of propionic acid was heated to 190° F., with stirring, under a nitrogen atmosphere. To the stirred mixture there was continuously added a dispersion comprised of 38.98 g mineral oil, 13.86 g isodecyl alcohol, 3.71 g butyl Carbitol and 43.28 g of lime (0.5498 moles) for about 33 minutes to produce a solution of calcium oleate in the mixture. The dispersion was added at a rate of about 3 g per minute. At this point in the reaction, the mixture tested basic with phenolphthalein (about 10–12 pH). Then, to the stirred mixture there was continuously added, over a period of about 3 hours and 56 minutes, a dispersion comprised of 276.25 g mineral oil, 98.23 g isodecyl alcohol, 26.31 g butyl Carbitol and 306.75 g lime (3.897 moles) while the mixture was being treated with carbon dioxide at 1.5 SCFH at 195–200° F. The dispersion was also added at a rate of about 3 g per minute. The basicity of the reaction was checked to maintain the basicity during the reaction. When the reaction mixture tested nearly neutral to phenolphthalein, the carbon dioxide addition was discontinued. The reaction mixture was then heated to 300° F. and a total of 99.36 g of water was removed via a Dean-Stark trap. The resulting product mixture was stirred and 24.00 g of filter aid (diatomaceous earth) was added. The product mixture was filtered with suction, as stated above in the description, at about 300 ml per 10 minutes, yielding a clear, amber, mobile liquid filtrate of overbased calcium oleate/carbonate which remained clear upon cooling to room temperature. The filtrate was analyzed to contain 10.4% Calcium by weight.

EXAMPLE 2

14% Overbased Calcium Oleate/Carbonate

A phenol-free overbased calcium oleate/carbonate containing 14% calcium by weight was made according to this Example. In a 3-liter resin kettle equipped with an overhead stirrer, two gas inlet tubes, a thermocouple, heating mantle and Dean-Stark trap with condenser, was added 1700 g of a 9.89% overbased calcium oleate/carboxylate made by the method of the previous example and 42.5 g of deionized water. The mixture was heated with stirring under a nitrogen atmosphere to a temperature of 195° F., and a slurry containing 385 g of hydrated lime (94% calcium hydroxide), 231 g of hydrocarbon oil, 96.25 g of isodecyl alcohol, and 57.75 g of butyl Carbitol was added at a rate of 3.42 g per minute over a 3 hour 45 minute period. After 5 minutes of slurry addition, carbon dioxide was added to the reaction at a rate of 1.2 standard cubic feet per hour. During the carbonation, a temperature of 195–200° F. was maintained and pH was monitored as in Example 1.

After the slurry addition was finished, the carbon dioxide addition was continued until the reaction mixture was neutral, as shown by a colorless sample when tested with phenolphthalein. The reaction mixture was then heated to 300° F. and both the water added and the water produced in the reaction was removed via the Dean-Stark trap. To the dehydrated reaction product was added 75 g of diatomaceous earth and the product was filtered with suction, as above in Example 1, yielding a clear, amber, mobile liquid filtrate of overbased calcium oleate/carboxylate which remained clear on cooling to room temperature. The filtrate was analyzed to contain 14.5% calcium by weight.

EXAMPLE 3

10% Overbased Calcium Oleate/Carbonate, GRAS Indirect Food Additive Formula

A phenol-free 10% overbased calcium oleate/carbonate containing only materials generally recognized as safe as indirect food additive was prepared as follows. A mixture of 520.6 g of oleic acid (1.85 moles), 522 g of Shellflex™ 6111 light mineral oil, 259 g of dodecyl alcohol, and 32.4 g of propylene glycol was heated to 180° F. and 2.0 g of propionic acid and 15.0 g of water was added. To the stirred reaction mixture there was continuously added a slurry comprised of 345.6 g of Shellflex™ 6111, 172.8 g of dodecyl alcohol, 21.6 g of propylene glycol, and 540 g of lime (94% available as calcium hydroxide) at a rate of 4.0 g per minute. After approximately 41 minutes of slurry addition, the oleic acid was neutralized and excess lime was present and partially dissolved to give an apparent pH of 11.4. Then carbon dioxide gas was passed into the reaction mixture through a subsurface addition tube at a rate of approximately 495 ml/minute to produce and maintain a pH of 10.5–11 for the duration of the slurry addition (approximately 5.25 hours), while maintaining the reaction temperature at 190–192° F. with mild cooling. When approximately 1080 g of slurry had been added, the slurry addition was turned off and the carbon dioxide addition was continued until the pH of the reaction dropped to 7.5 (approximately 7 minutes). The reaction was carefully placed under 22.5 inches of vacuum and heated to 310° F. over a 1.75-hour period while removing the added water and the water of reaction via a Dean-Stark tube. The reaction was held at 310° F. and 30 g of diatomaceous earth filter aid was added. The product was filtered hot with suction as stated in the previous example at a rate of 545 ml per 10 minutes, yielding a clear, yellow-amber mobile filtrate of overbased calcium oleate/carbonate which remained clear on cooling to room temperature. The filtrate was analyzed to contain 10.5% calcium by weight. The infrared spectrum of the material showed a peak at 864 reciprocal centimeters, characteristic of amorphous calcium carbonate.[1]

[1] The physical state of the calcium carbonate in the materials prepared in the examples was analyzed by X-ray powder pattern for crystallinity and by infrared spectra. Amorphous calcium carbonate has an infrared absorption at 864 reciprocal centimeters, according to a paper "Infrared Spectra of Amorphous and Crystalline Calcium Carbonate" by Andersen and Brecevic, Acta Chemica Scandinavica 45 (1991) 1018–1024. The other crystalline polymorphs of calcium carbonate, calcite, aragonite and vaterite have corresponding infrared absorptions at 877, 856, and 877 reciprocal centimeters, respectively.

EXAMPLE 4

15% Overbased Calcium Oleate/Carbonate

A highly overbased calcium oleate/carbonate containing 15.4% calcium by weight was produced by the following procedure. To a mixture of 1700 g of an 11.4% overbased calcium oleate/carbonate liquid produced according to the previous example was added 50 g of water and the mixture was heated to 190° F. under stirring at 1000 rpm.

To the mixture was added a 720 g portion of a slurry made from 500 g of lime (94% available as calcium hydroxide), 320 g of Shellflex™ 6111 light mineral oil, 160 g of dodecyl alcohol, and 20 g of propylene glycol at a rate of 3.97 g per minute over a 3 hour 40 minute period. After 2 minutes of slurry addition, carbon dioxide gas was introduced to the reaction mixture through a subsurface addition tube at a rate to produce and maintain the apparent pH of the reaction mixture at a value of 10.5–11 (approximately 450–550 ml/minute). After the time required to add the required amount of lime slurry passed, the slurry addition was discontinued and the carbon dioxide addition continued until the pH of the reaction fell to 7.5 (about 10 minutes). The reaction was then heated under a vacuum of 22.5" while heating slowly to 310° F. The water added and the water of reaction was removed via a Dean-Stark trap. The reaction mixture was then filtered through a bed of diatomaceous earth (filter aid) to give a clear, amber mobile filtrate of a highly overbased calcium oleate/carbonate. The material was analyzed to contain 15.4% calcium by weight. The infrared spectrum of the material showed a characteristic peak for amorphous calcium carbonate at 864 reciprocal centimeters.

EXAMPLE 5

14% Overbased Strontium Oleate/Carbonate

A phenol-free strontium oleate/carbonate containing about 14% strontium was prepared by the following procedure. A mixture of 413 g of oleic acid, 600 g of Shellflex™ 6111 light mineral oil, 300 g of isodecyl alcohol, 40 g of butyl carbitol, and 4 g of triethylene glycol was heated to 176° F., and 1000 g of strontium hydroxide octahydrate was added. The reaction mixture was heated to 275° F. over a 2.5-hour period, while removing 550 g of water via a Dean-Stark trap with the aid of a nitrogen sparge at 2.0 SCFH. After the rate of water removal slowed, the nitrogen sparge was turned off, and carbon dioxide gas was added to the reaction via a subsurface addition tube at a rate of 450 ml/minute, and the water formed was continually removed. After 7 hours of carbon dioxide addition at 250–275° F., the carbon dioxide was turned off, the temperature of the reaction was raised to 300° F. and the remaining water was removed with the assistance of a nitrogen sparge at 2.0 SCFH. The reaction was then filtered hot with suction with the assistance of filter aid, yielding the overbased strontium oleate carbonate as a light yellow, clear mobile liquid. The product was analyzed to contain 14.25% strontium by weight.

EXAMPLE 6

4.5% Overbased Magnesium Oleate/Carbonate

A phenol-free magnesium oleate/carbonate containing about 4.5% magnesium was prepared by the following procedure. A mixture of 529.3 g of oleic acid, 600 g of Shellflex™ 6111 light mineral oil, 400 g of isopropyl alcohol, 350 g of isodecyl alcohol, 400 g of water was heated to 140° F. and 400 g of magnesium hydroxide was added. The neutralization of the acid with the magnesium hydroxide caused the temperature to rise to 167° F. Carbon dioxide gas was passed into the reaction mixture through a subsurface addition tube at a rate of 225 ml/minute for 6 hours, during which time the temperature was gradually raised to 223° F. and 720 ml of a mixture of water and isopropyl alcohol was removed. The temperature was raised to 305° F. and the remaining water was removed with the assistance of the carbon dioxide addition. The carbon dioxide addition was stopped, and the hot reaction mixture was filtered with suction with the assistance of filter aid, giving the overbased magnesium product as a clear light yellow mobile liquid. The product was analyzed to contain 4.5% magnesium by weight.

EXAMPLE 7

21.38% Overbased Amorphous Calcium Oleate/Carbonate Powder

To 1000 g of rapidly stirred isopropyl alcohol was added 200 g of an overbased calcium oleate/carbonate liquid containing 10.5% calcium by weight (product prepared as in Example 3) in a steady stream over a period of 5 minutes. The mixture was stirred at room temperature for 1 hour, and then filtered with suction. The filter cake was washed with 2×100 g of isopropyl alcohol, sucked as dry as possible, and then allowed to dry at room temperature overnight. The powder obtained showed no crystalline nature by x-ray powder pattern, and dispersed easily in mineral oil to give a clear, isotropic, non-viscous dispersion. The powder was found to contain 21.38% calcium by weight. An infrared spectrum of the powder (nujol mull) showed a peak at 866 reciprocal centimeters, characteristic of amorphous calcium carbonate.

EXAMPLE 8

20.2% Overbased Amorphous Calcium Oleate/Carbonate Powder

A powdered overbased amorphous calcium oleate/carbonate was prepared according to the following example. To 1500 g of isopropyl alcohol, rapidly stirred and heated to reflux, 500 g of overbased calcium oleate/carbonate liquid containing 9.76% calcium by weight (product of example 1 above) was added over a 15-minute period. The mixture was allowed to reflux a further ½ hour, and then allowed to cool to 90° F. and filtered with suction. The collected solids were washed with 2×125 g of isopropyl alcohol, and sucked as dry as possible. The solid product was allowed to dry at room temperature overnight and yielded 262 g of an off-white solid, which was analyzed to contain 20.2% calcium by weight. The material was easily dispersed in mineral oil at 70% solid to give a clear, mobile dispersion with a calcium content of 13.83% by weight. An infrared spectrum of the powder (nujol mull) showed a peak at 866 reciprocal centimeters, characteristic of amorphous calcium carbonate. The powder particles, dispersed in mineral spirits, showed a mean particle diameter of 0.112 microns.

EXAMPLE 9

28% Overbased Amorphous Calcium Oleate/ Carbonate Powder

A powdered overbased amorphous calcium oleate/carbonate powder was prepared according to the following example. 200 g of an overbased calcium oleate/carbonate liquid dispersion containing 15.4% calcium by weight (prepared by Example 4, above) was added in a steady stream to 1000 g of rapidly stirred isopropyl alcohol in a 5-minute period. The mixture was stirred at room temperature for an additional hour, then filtered with suction, washed with 2×100 ml of isopropyl alcohol, and sucked as dry as possible. The product was allowed to dry in air at room temperature overnight, yielding a free-flowing off-white powder that was analyzed to contain 28% calcium by weight. An infrared spectrum of the powder (nujol mull) showed a peak at 866 reciprocal centimeters, characteristic of amorphous calcium carbonate. An X-ray powder pattern showed only broad peaks, with no peaks from calcite (crystalline calcium carbonate). The powder, dispersed in mineral spirits, showed a mean particle diameter of 0.0566 microns.

EXAMPLE 10

30% Overbased Amorphous Barium Oleate/ Carbonate

A phenol-free overbased amorphous barium oleate/carbonate was prepared according to the following example. A mixture of 502.5 g of oleic acid, 581 g of HVI mineral oil, 200.0 g of Epal™ 14–18 (a mixture of aliphatic alcohols containing 14 to 18 carbon atoms), 102 g of butyl carbitol (diethylene glycol monobutylether and 10.2 g or triethylene glycol was heated to 178° F. under a slow stream of nitrogen. To the heater reaction mixture was added 1034.1 g of barium hydroxide monohydrate in three increments over a 45-minute period. The temperature of the reaction mixture was then raised to 280° F. over a one-hour period, and 75.6 g of water was removed via a Dean-Stark trap with the aid of the nitrogen flow of 2 SCFH. The nitrogen flow was reduced to 1 SCFH and carbon dioxide was added via a subsurface addition tube at a rate of about 300 ml/min over a 5½ hour period, during which time the temperature was gradually raised from 280° F. to 300° F. and water was removed via a Dean-Stark trap at the approximate rate of 7.5 g every 15 minutes after 2 hours.

At the end of the carbon dioxide addition time, the reaction was carefully placed under 22 inches of vacuum and the remaining water was removed, along with a small amount of butyl carbitol. The total water removed was 210 g. After 30 minutes, the vacuum was released, and 40 g of filter aid (diatomaceous earth) was added. The mineral was filtered by suction to give a clear, amber, mobile liquid which was analyzed to contain 29.7% barium by weight.

EXAMPLE 11

45.2% Overbased Amorphous Barium Oleate/ Carbonate Powder

A phenol-free overbased barium oleate/carbonate containing 29.7% barium by weight (prepared by Example 10) was poured in a slow stream in 5 minutes into 1000 g of isopropyl alcohol under rapid stirring. The mixture was allowed to stir at room temperature for 1 hour, and then filtered with suction, washed with 2×100 g of isopropyl alcohol, sucked as dry as possible then allowed to dry in air overnight. The product, an off-white powder, as analyzed to contain 45.2% barium by weight.

EXAMPLE 12

45.5% Overbased Amorphous Barium Oleate/ Phenate/Carbonate Powder

A phenol-containing overbased amorphous barium oleate/phenate/carbonate liquid containing 45.5% barium was prepared according to Example 10 with the addition of phenol to the reaction mixture, as, for example, disclosed in U.S. Pat. No. 5,830,935. 200 g of this overbased barium oleate/phenate/carbonate was added to 1000 g of rapidly stirred isopropyl alcohol at room temperature over a 5-minute period. The mixture was allowed to stir for ½ hours, then was filtered with suction, washed 2×100 g of isopropyl alcohol, sucked as dry as possible, and allowed to dry in air. The product, a pink powder, was analyzed to contain 45.5% barium by weight.

The above description provides a disclosure of particular embodiments of the invention and is not intended for the purpose of limiting the same thereto. As such, the invention is not limited to only the above described embodiments, rather, it is recognized that one skilled in the art would understand alternative embodiments in view of the above description that fall within the scope of the invention.

What is claimed is:

1. A powdered overbased amorphous alkaline earth metal salt of a fatty acid consisting essentially of
   isolated solid agglomerated micelles of a complexed salt of an amorphous alkaline earth metal salt from the group consisting of carbonate, sulfate, sulfide and sulfite, complexed with an amorphous alkaline earth metal carboxylate of a fatty acid.

2. The powdered salt of claim 1 wherein said micelles are agglomerates of the complexed salt having particle sizes the order of about 50 microns.

3. The powdered salt of claim 1 wherein said fatty acid is a $C_{12}$–$C_{22}$ fatty acid.

4. The powdered salt of claim 1 wherein said fatty acid is oleic acid.

5. The powdered salt of claim 1 wherein said alkaline earth metal is selected from the group consisting of calcium, barium, magnesium and strontium.

6. The powdered salt of claim 1 wherein said alkaline earth metal is calcium.

7. The powdered salt of claim 1 wherein the overbased alkaline earth salt is calcium oleate/carbonate.

8. The powdered salt of claim 1 which is dispersed in a liquid hydrocarbon to form a haze free liquid.

9. The powdered salt of claim 8 wherein said liquid hydrocarbon is selected from the group consisting of an oil, mineral spirits and non-aromatic hydrocarbons.

10. The powdered salt of claim 1 containing about 8% to about 70% by weight of alkaline earth metal.

11. The powdered salt of claim 10 wherein the alkaline earth metal is calcium which is contained in an amount of about 8% to about 30% by weight.

12. A powdered overbased amorphous calcium salt of a fatty acid consisting essentially of
    isolated solid agglomerated micelles of a complexed salt of an amorphous calcium carbonate complexed with amorphous calcium carboxylate of a fatty acid.

13. The powdered salt of claim 12 which is dispersible in a liquid hydrocarbon.

14. The powdered salt of claim 12 wherein said micelles are on the order of about 50 microns.

15. The powdered salt of claim 13 wherein the liquid hydrocarbon is an oil.

16. The powdered salt of claim 13 wherein the liquid hydrocarbon is selected from the group consisting of an oil, mineral spirits and non-aromatic hydrocarbons.

17. The powdered salt of claim 12 wherein said fatty acid is a $C_{12}$–$C_{22}$ fatty acid.

18. The powdered salt of claim 12 wherein said fatty acid is oleic acid.

19. The powdered salt of claim 12 containing about 8% up to about 70% by weight calcium.

20. The powdered salt of claim 12 wherein calcium is contained in an amount of at least about 15% to about 30% by weight.

21. A process for preparing a powdered overbased amorphous alkaline earth metal salt of a fatty acid comprising
    reacting an alkaline earth metal base and a fatty acid with an equivalent ratio of metal base to fatty acid being greater than 1:1 in the presence of liquid hydrocarbon,
    acidifying the mixture to produce an amorphous alkaline earth metal salt from the group consisting of carbonate, sulfate, sulfide and sulfite complexed with an amorphous alkaline earth metal carboxylate of the fatty acid in said liquid hydrocarbon,
    precipitating from said liquid hydrocarbon solid particles of an amorphous alkaline earth metal salt from the group consisting of carbonate, sulfate, sulfide and sulfite complexed with an amorphous alkaline earth metal carboxylate of a fatty acid, and
    isolating said solid particles in the form of powdered overbased amorphous alkaline earth metal salt.

22. The process of claim 21 comprising isolating said particles by filtration.

23. The process of claim 21 wherein said precipitation step is conducted by adding a solvent for said liquid hydrocarbon.

24. The process of claim 21 wherein said fatty acid is a $C_{12}$–$C_{22}$ fatty acid.

25. The process of claim 21 wherein said fatty acid is oleic acid.

26. The process of claim 22 wherein the particles are dried.

27. The process of claim 21 wherein said alkaline earth metal is selected from the group consisting of calcium, barium, magnesium and strontium.

28. The process of claim 21 wherein said alkaline earth metal is calcium and the mixture is acidified by carbonating to form an amorphous calcium carbonate complexed with an amorphous alkaline earth metal carboxylate.

29. The process of claim 28 wherein the powdered overbased salt is calcium oleate/carbonate.

30. The process of claim 23 wherein said solvent is an alcohol.

31. The process of claim 21 wherein said reaction is conducted in the presence of an alcohol promoter.

32. The process of claim 31 wherein the alcohol has 8 to 14 carbon atoms.

33. The process of claim 31 which further contains a glycol or a glycol ether.

34. The process of claim 33 wherein the glycol or glycol ether is selected from the group consisting of diethylene glycol monobutyl ether, triethylene glycol, propylene glycol, dipropylene glycol, diethylene glycol monomethyl ether, ethylene glycol monobutyl ether, and mixtures thereof.

35. The process of claim 21 by reacting on the basis of the final reaction mixture an amount of an alkaline earth metal base selected from the group consisting of about 15–30% calcium hydroxide, about 12–24% magnesium hydroxide, about 25–50% strontium hydroxide, and about 35–50% barium hydroxide, and mixtures thereof.

36. The process of claim 35 wherein the alkaline earth metal base is calcium hydroxide and the fatty acid is oleic acid.

37. The process for preparing a powdered overbased amorphous calcium oleate/carbonate comprising
    reacting calcium hydroxide base and oleic acid with an equivalent ratio of the base to the acid being greater than 1:1 in the presence of a mixture of liquid hydrocarbon and catalyst,
    carbonating the mixture to produce amorphous calcium carbonate,
    adding during carbonation a dispersion of calcium hydroxide, liquid hydrocarbon and cosurfactant aliphatic alcohol having at least 8 carbon atoms in relative amounts at a controlled rate of calcium hydroxide addition to produce a liquid reaction product,
    removing water from the reaction product to provide an overbased amorphous calcium oleate/carbonate in said liquid hydrocarbon,
    precipitating from said liquid hydrocarbon solid particles of an amorphous calcium carbonate complexed with an amorphous alkaline earth metal carboxylate of a fatty acid, and
    isolating said solid particles in the form of powdered overbased amorphous alkaline earth metal salt.

38. The process of claim 37 wherein the catalyst is selected from the group consisting of propionic acid, citric acid, acetic acid and adipic acid.

39. The process of claim 37 wherein the cosurfactant is an aliphatic alcohol having 8 to 14 carbon atoms.

40. The process of claim 39 wherein the alcohol selected is isodecanol in the presence of diethylene glycol monobutyl ether and triethylene glycol.

41. The process of claim 37 wherein after the addition of the dispersion and carbonation with carbon dioxide the mixture contains
    about 15–30% calcium oleate,
    about 9–35% calcium carbonate, about 30–35% hydrocarbon oil, about 15–18% isodecanol, and about 4–6% glycol or glycol ether.

42. The process of claim 41 wherein the dispersion contains about 40–50% calcium hydroxide, about 25–40% hydrocarbon oil, about 10–25% isodecanol and about 0–10% glycol or glycol ether.

43. The process of claim 37 wherein a solvent for said liquid hydrocarbon is added for precipitating said solid particles.

44. The process of claim 43 wherein said solvent is an alcohol selected from the group of isopropyl alcohol, methanol, ethanol, propanol, butanol, and glycol ethers.

45. The process of claim 43 wherein the particles are isolated by filtration and drying.

46. The process of claim 37 wherein said particles are on the order of about 50 microns.

* * * * *

UNITED STATES PATENT AND TRADEMARK OFFICE
CERTIFICATE OF CORRECTION

PATENT NO. : 6,639,090 B2
DATED : October 28, 2003
INVENTOR(S) : Chester E. Ramey et al.

It is certified that error appears in the above-identified patent and that said Letters Patent is hereby corrected as shown below:

Column 3,
Lines 51-52, change "dispersion or slurry of base du ring carbonation" to -- dispersion of slurry of base during carbonation --

Column 8,
Line 67, after "preferably has", insert -- the following composition ranges: --

Column 16,
Line 32, change "stir for ½ hours" to -- stir for 1½ hours --

Signed and Sealed this

Twenty-second Day of June, 2004

JON W. DUDAS
*Acting Director of the United States Patent and Trademark Office*